US008586164B2

(12) United States Patent
Weber et al.

(10) Patent No.: US 8,586,164 B2
(45) Date of Patent: Nov. 19, 2013

(54) NAIL STRIPS HAVING A CROSSLINKED POLYMER TOP COAT

(75) Inventors: Susan M. Weber, Pond Eddy, NY (US); Christian J. Lee, Parsippany, NJ (US); Maha Raouf, Franklin Lakes, NJ (US)

(73) Assignee: Avon Products, Inc, New York, NY (US)

( * ) Notice: Subject to any disclaimer, the term of this patent is extended or adjusted under 35 U.S.C. 154(b) by 789 days.

(21) Appl. No.: 11/884,996

(22) PCT Filed: Dec. 29, 2005

(86) PCT No.: PCT/US2005/046769

§ 371 (c)(1), (2), (4) Date: Dec. 4, 2008

(87) PCT Pub. No.: WO2006/071768

PCT Pub. Date: Jul. 6, 2006

(65) Prior Publication Data

US 2009/0233031 A1 Sep. 17, 2009

Related U.S. Application Data

(60) Provisional application No. 60/640,030, filed on Dec. 29, 2004.

(51) Int. Cl.

| | |
|---|---|
| ***B32B 9/00*** | (2006.01) |
| ***B32B 27/06*** | (2006.01) |
| ***B32B 37/12*** | (2006.01) |
| ***B44C 1/165*** | (2006.01) |
| ***A45D 29/18*** | (2006.01) |

(52) U.S. Cl.

USPC ........... 428/40.1; 428/41.6; 428/914; 132/73; 132/285; 156/60; 156/230; 156/278

(58) Field of Classification Search

USPC ........ 428/40.1, 41.6, 914; 427/385.5; 132/73, 132/285; 156/60, 196, 230, 235, 278

See application file for complete search history.

(56) References Cited

U.S. PATENT DOCUMENTS

| | | | | |
|---|---|---|---|---|
| 2,162,155 | A | 6/1939 | Calvin | |
| 2,688,331 | A | 9/1954 | Bogoslowsky | |
| 2,816,555 | A | 12/1957 | Klump | |
| 2,979,061 | A * | 4/1961 | Greenman et al. | 132/73 |
| 3,875,950 | A * | 4/1975 | Gens | 132/200 |
| 3,993,084 | A | 11/1976 | Cullen | |
| 4,903,840 | A * | 2/1990 | So | 206/581 |
| 4,947,876 | A | 8/1990 | Larsen | |
| 5,415,903 | A * | 5/1995 | Hoffman et al. | 428/15 |
| 5,525,389 | A * | 6/1996 | Hoffmann et al. | 428/41.5 |
| 6,277,358 | B1 | 8/2001 | Calello | |
| 2003/0209249 | A1 * | 11/2003 | Park | 132/73 |
| 2004/0079381 | A1 | 4/2004 | Han | |
| 2004/0161564 | A1 * | 8/2004 | Truog | 428/40.1 |
| 2005/0199253 | A1 * | 9/2005 | Fiore et al. | 132/73 |
| 2005/0255061 | A1 | 11/2005 | Park | |

FOREIGN PATENT DOCUMENTS

| | | | |
|---|---|---|---|
| EP | 1371693 | A2 | 12/2003 |
| WO | 88/02226 | | 4/1988 |
| WO | 2005/112874 | A1 | 12/2005 |

* cited by examiner

*Primary Examiner* — Patricia Nordmeyer

(74) *Attorney, Agent, or Firm* — David M. Joyal; Joan M. McGillycuddy; Brian C. Remy

(57) ABSTRACT

There is provided a nail enamel strip having a substrate layer and a nail enamel film with one or more nail enamel layers, at least one of the nail enamel layers having a cross-linked polymer. The nail enamel film is detachably adhered to the substrate layer. Further, there is provided a method for making the nail enamel strips, and a method of applying the nail enamel strip on a nail.

30 Claims, No Drawings

NAIL STRIPS HAVING A CROSSLINKED POLYMER TOP COAT

CROSS-REFERENCE TO A RELATED APPLICATION

The present application claims priority on U.S. Provisional Patent Application No. 60/640,030, filed Dec. 29, 2004, which is incorporated by reference herein in its entirety.

BACKGROUND OF THE INVENTION

1. Field of the Invention

The present invention relates to fingernail and toenail strips and methods for making and using the same. More particularly, the present invention relates to self-adhesive nail enamel strips for fingernails and toenails that have a cross-linked nail enamel layer to provide long-lasting wear and a shiny appearance, without the need of ultraviolet (UV) light curing and, thus, professional assistance. That is, the nail enamel strips include a layer that has a pre-cured, cross-linked polymer.

2. Description of the Related Art

When fingernails or toenails are coated with liquid nail polish, the liquid polish is dried by exposure to the air. While the polish on the nail is left to dry, the nails must not come into contact with any object, or else the nail coat becomes smudged or smeared. The problem of waiting for the polish to dry is accentuated for French manicuring or polishing because the treatment requires at least two layers of nail polish. In a French manicure, a first coat of liquid nail polish is applied to the nails, and must dry before the application of a second layer of liquid polish that creates a fanciful design. Likewise, the second layer must also dry before the nail can be used. Such nail treatment clearly requires a great deal of time for the necessary drying.

These problems have been somewhat dissipated by the use of a semi-solid form, or finger strip, nail coat techniques. A finger enamel layer that can be adhesively secured to the nail substantially reduces the time involved to coat or polish the nail. Further, this technique eliminates the accidental contact between the liquefied nail polish and the user's skin.

Nail enamel strips are known in which a pliable nail enamel film is peelably or detachably provided on a substrate. The pliable nail enamel film has an adhesive layer and one or more nail enamel layers, for example, a top coat layer and a base coat layer. Each enamel layer may have different ingredients depending where the layer is positioned, such as a top layer or a base layer. Other such films have a single nail enamel layer. These nail enamel strips are sealed in an airtight envelope or package to maintain the pliability of the nail enamel film. The package is opened when it is desired to use the product. The nail enamel film is peeled from the substrate and then placed by the user onto a nail. The nail enamel film is sufficiently pliable that it can conform to the contours of a user's nail. After application of the nail enamel film to the user's nail, the nail enamel film is allowed to dry in air to allow residual solvent to evaporate.

Liquid nail polish products are also known that contain a polymeric film former that is curable by UV light. These liquid nail polish products further have a cross-linking agent to effect the cross-linking of the cross-linkable polymer. The nail polish treatment that is provided by these liquid products is long-lasting, wear-resistant, and has a good shine. However, pliable nail enamel strips that incorporate a cross-linked polymer are not known.

In light of the foregoing, it is desired to have a nail enamel strip incorporating a nail enamel layer having a cross-linked polymer, i.e., a cross-linkable polymer that is already cross-linked.

SUMMARY OF THE INVENTION

It is an object of the present invention to provide nail enamel strips that impart a long-lasting wear and shine to fingernails and toenails.

It is another object of the present invention to provide nail enamel strips that require minimal drying/application time.

It is still another object of the present invention to provide a nail enamel film that has a cross-linked polymer for long-lasting wear and shine.

It is a further object of the present invention to provide a nail enamel film for imparting long-lasting wear and shine without the need of UV light treatment in the salon, thereby eliminating the need for application in a nail salon.

According to this and other objects and advantages of the present invention, there are provided nail strips for imparting long-lasting wear and shine to the fingernails and toenails. There are also provided methods for making and applying such nail strips. The nail enamel strip has a nail enamel film that has one or more nail enamel layers that provide the desired effects, such as long-lasting wear capabilities and shine, without the use of a UV light source. At least one nail enamel layer, preferably the topmost layer in any multi-layer film, has a cross-linked polymer. The cross-linking of the polymer takes place during the manufacture of the nail strip, and any suitable curing means may be used, typically UV curing or thermal curing.

One preferred nail enamel strip according to the present invention has a first nail enamel layer and a second enamel layer. The first enamel layer has a base coat layer with one or more nail polish pigments, preferably without cross-linked polymers. The second nail enamel layer has a transparent top coat layer, preferably with one or more cross-linked polymers and without pigments.

The present invention also provides methods for making such nail enamel strips. The method has the steps of a) incorporating one or more cross-linkable polymers into a nail enamel composition, typically in further combination with a cross-linking agent, b) spraying or otherwise distributing the composition on a substrate to form a nail enamel layer, and c) curing the nail enamel layer to initiate cross-linking of the cross-linkable polymer to form a cross-linked polymer. During curing, the nail enamel layer is preferably exposed to a UV light source, although thermal curing, i.e., heat curing, may also be used.

Preferably, a nail enamel base coat layer has one or more nail pigments or colorants, and a transparent nail enamel top coat layer has one or more cross-linked polymers.

Still further, the present invention provides methods for imparting long-lasting wear and shine to fingernails and/or toenails. One such method includes applying the nail enamel strips to the fingernails and/or toenails.

DETAILED DESCRIPTION OF THE INVENTION

The present invention provides nail enamel strips. Each nail enamel strip has a nail enamel film that imparts long-lasting wear and shine once applied to a fingernail and/or toenail. Thus, a consumer desires such a nail enamel strip because the consumer can apply the nail enamel film of the nail strip at home.

Each nail enamel strip of the present invention is an article of manufacture that has a substrate or substrate layer, an adhesive layer and a nail enamel film removably (i.e., peelably) provided onto the substrate. The nail enamel film has one or more nail enamel layers.

In a first embodiment, the nail strip has a substrate, an adhesive layer, and a nail film having one nail enamel layer, namely, a base coat layer. The base coat layer has one or more cross-linked polymers, optionally one or more non-cross-linked polymers and, if desired, one or more pigments or colorants.

In a second embodiment, the nail strip has a substrate, an adhesive layer, and a nail film with a two or more nail enamel layers, preferably two nail enamel layers. In the preferred two nail enamel layer embodiment, there is a first or base coat layer that has one or more pigments, and a second or top coat layer that has one or more cross-linked polymers. Most preferably, the base coat layer does not have any cross-linked polymers and the top coat layer does not have any pigments. Also, the top coat is transparent or virtually transparent so that the pigment in the base coat layer is visible with minimal loss in the observed color. Either the top coat layer or the base coat layer may have one or more non-cross-linked polymers.

In a third embodiment, the more preferred embodiment, the nail strip has a substrate, an adhesive layer, and a nail film with a three nail enamel layers. As will be discussed below, the three nail enamel layers are a first or bottom or base coat layer in contact with the adhesive layer, a second or middle coat layer, and a top coat layer having the cross-linked polymer.

In all embodiments, it is preferred that the nail strip include a removable protective layer overlying the top coat layer that must be removed before the nail film is applied to a nail. The protective layer is conveniently an acetate resin layer or other known protective barrier. The protective barrier prevents damage to the top coat layer of the nail enamel film.

In the two nail enamel layer embodiment, the base coat layer is present about 20 weight percent (wt %) to about 80 wt % based on the total weight of the nail film. Likewise, the top coat layer is present about 20 wt % to about 80 wt % based on the total weight of the nail film.

The substrate in all embodiments is preferably a paper or other cellulosic material. Preferably, the paper or other cellulosic material is coated on one of its two sides with a silicon-based release coating. Deposited on the top of the release coat is the adhesive layer. The adhesive layer remains on the substrate and permits the nail enamel film to be easily peelable from the substrate, and there is a sufficient residual adhesive on the bottom surface of the nail film that allows it to adhere to the nail.

The adhesive layer assists in having the nail film, namely the nail enamel layers, remain on the nail strip prior to use, and in securing the nail film to the user's nail.

The adhesive of the adhesive layer can be any water-based or solvent-based adhesive that is not harmful to skin. An adhesive can be, but is not limited to, acrylic copolymers.

In the present invention, "cross-linkable polymer" means a polymer that can be cross-linked by curing using UV light or thermal energy, or curing in the presence of a cross-linking agent by UV light or thermal energy. Also, the term "cross-linked polymer" is inclusive of cross-linkable polymers that have been cross-linked.

The cross-linked polymers that can be used in all embodiments of the present invention are cross-linked by UV light or thermal curing, preferably by UV light. In some instances, depending on the polymer, cross-linking agents are used in conjunction with the curing. With cross-linking agents, the curing can be by UV light or thermal energy, but preferably is by UV light.

Useful cross-linking agents include, but are not limited to, one or more organofunctional silanes, titanates, photoactive oligomers, or any combinations thereof.

The cross-linked polymers that can be used in the present invention include, but are not limited to, nitrocellulose, acrylic copolymer, polyamide, polyurethane, ethyl methylacrylate, dimethacrylate, ethylcyanoacrylate, polymethylmethacrylate, urethane methacrylate oligomer, methacylate monomer, methacrylic acid, organofunctional silane, titanate, photoactive oligomer, monomethyl ether hydroquinone (MEHQ), or any combinations thereof. These cross-linked polymers may have film-forming properties.

The cross-linking of polymers is effectuated during manufacture of the nail enamel strips.

As used in the present invention, the recited wt % of an ingredient is the wt % of that ingredient in the layer that contains that ingredient, unless indicated as a percentage of the nail film (i.e., all layers of the nail film) and as manufactured (i.e., just after removal from the airtight package and before evaporation of any volatiles contained in the layer).

The amount of the cross-linked polymer depends on the nature of the nail enamel layer in which it is incorporated, and accordingly may vary over broad concentration ranges. Generally, the cross-linked polymer, which is present in at least one of the nail enamel layers of the nail enamel film, preferably, the topmost layer, is present in an amount about 5 wt % to about 99 wt % based on total weight of the nail enamel layer. When the nail enamel layer having the cross-linked polymer is to provide a transparent film, the enamel layer has the cross-linked polymer present in an amount about 20 wt % to about 99 wt %, preferably about 65 wt % to about 97 wt %, and more preferably about 75 wt % to about 95 wt %, based on total weight of the nail enamel layer. When the nail enamel layer having the cross-linked polymer is to impart a color, the nail enamel layer has the cross-linked polymer present in an amount about 10 wt % to about 90 wt %, preferably about 40 wt % to about 85 wt %, and more preferably about 65 wt % to about 75 wt %, based on the total weight of the nail enamel layer.

The nail enamel film may have in any layer, preferably the nail enamel layer having the cross-linked polymer, one or more plasticizers, one or more adjuvant film-forming polymers, one or more thickeners or leveling agents, and one or more optional ingredients.

In addition, the nail enamel films may have a residual amount of solvent that is not evaporated from the nail enamel layer during the manufacturing process. The residual amount of solvent is preferably about 1 wt % to about 15 wt %, more preferably about 3 wt % to about 12 wt %, and most preferably about 5 wt % to about 10 wt %, based on the total weight of the nail enamel layer. This residual solvent ensures that each of the nail enamel layers, and hence of the nail enamel film itself, will not be dry when used, and will have sufficient pliability so that the nail enamel film can be peeled from the substrate and placed by the user on a nail.

Suitable solvents for use in the embodiments of the present invention include, but are not limited, to acetic acid esters, such as methyl-, ethyl-, butyl-, amyl- or 2-methoxyethyl acetate; ketones, such as methyl ethyl ketone, methyl isobutyl ketone; isopropyl acetate; hydrocarbons, such as toluene, zylene, p-xylene, hexane or heptane; aldehydes having 5 to 10 carbon atoms; ethers having 3 carbon atoms; lower alcohols, such as ethanol and isopropyl alcohol; or any combination thereof.

An adjuvant film-forming polymer is a film-forming polymer that is not cross-linked. Suitable adjuvant film-forming polymers for use in the present invention include, but are not limited to, nitrocellulose, polyacrylate homopolymer or copolymer, polyester, polyurethane, carbon-based resin, silicone resin, ethylcellulose, polyvinylbutyral, polyamide, polyester, or any combinations thereof. Preferably, the adjuvant film-forming polymer is nitrocellulose, polyurethane, polyacrylate, or any combination thereof. The adjuvant film-forming polymer may be incorporated in either the nail enamel layer having the cross-linked polymer, but preferably are present in the nail enamel layer that does not have the cross-linked polymer. Although certain of these adjuvant film-forming polymers are cross-linkable (while others are not cross-linkable), they can be incorporated in a nail enamel film without cross-linking as noted above. Thus, the nail enamel layer that is the base coat layer (which could but usually would not have a cross-linked polymer) could have an adjuvant film-forming polymer that is potentially cross-linkable with a cross-linking agent that is excluded from such layer.

The preferred process for cross-linking with UV light is as follows. In the first pass through the process, a base coat composition is applied to the substrate and then allowed to substantially dry. On drying, the solvent in the base coat layer has substantially evaporated. There is no UV curing needed in this pass unless a cross-linkable polymer is present in the base coat composition. In the next or second pass through the process, the top coat is applied and the top coat is UV cured. The UV lamp or source could be positioned at the last stage of this process. The UV exposure during the second pass will improve adherence between the base coat layer and the topmost layer because of inter-layer cross-linking at the interface of the layers and will not adversely affect the resultant product. For certain classes of cross-linking agents that are activated by heat, the temperature at which each class is activated will vary. Preferred cross-linking agents are those that are activated at the temperature used to evaporate the solvents.

When present, and in a nail enamel film having a pigment or color, the one or more adjuvant film-forming polymers are present in an amount about 1 wt % to about 95 wt % based on the total weight of the nail enamel layer. More preferably, the one or more adjuvant film-forming polymers are present at about 5 wt % to about 75 wt % based on the total weight of the nail enamel layer. Most preferably, the one or more adjuvant film-forming polymers are present in an amount about 10 wt % to about 50 wt % based on the total weight of the nail enamel layer.

When present and in a nail enamel film that is clear (without pigment or color), the one or more adjuvant film-forming polymers are present in an amount about 1 wt % to about 95 wt % based on the total weight of the nail enamel layer. More preferably, the one or more adjuvant film-forming polymers are present in an amount about 5 wt % to about 90 wt % based on the total weight of the nail enamel layer. Most preferably, the one or more adjuvant film-forming polymers are present in an amount about 10 wt % to about 85 wt % based on the total weight of the nail enamel layer.

Suitable plasticizers for use in the present invention include, but are not limited to, one or more citrate esters, phthalates, sulfonamides, or any combinations thereof.

The one or more plasticizers are present in an amount about 1 wt % to about 35 wt % based on the total weight of the nail enamel layer. More preferably, the one or more plasticizers are present in an amount about 5 wt % to about 30 wt % based on the total weight of the nail enamel layer. Most preferably, the one or more plasticizers are present in an amount about 10 wt % to about 25 wt % based on the total weight of the nail enamel layer. The plasticizer does not evaporate substantially even in the nail film after it has dried on the nail. The plasticizer acts to prevent the film from becoming so brittle that the film would chip or crack.

In the first preferred embodiment (or one enamel layer nail film embodiment) of the present invention, the one nail enamel layer may have one or more pigments or colorants to provide color and/or aesthetic effects. In the second preferred embodiment (or two nail enamel layer nail film embodiment) of the present invention, the one or more pigments or colorants are in the second or topmost layer, and again provide color and/or aesthetic effects.

Suitable pigments or colorants for use in the present invention include, but are not limited to, inorganic pigments, such as, titanium dioxide, zirconium oxide and cerium oxide, zinc oxide, iron oxide, chromium oxide, ferric blue oxide; organic pigments, such as, carbon black; barium lakes, strontium lakes, calcium or aluminum lakes; mica; mica coated with pearlescent agents, such as titanium oxide, iron oxide, natural pigment, or bismuth oxychloride; or any combinations thereof. Pigments and insoluble lakes are preferred.

Preferably, the pigment-containing layer has one or more pigments in an amount about 5 wt % to about 50 wt % based on the total weight of the layer. More preferably, the pigment-containing layer has one or more pigments in an amount about 5 wt % to about 30 wt % based on the total weight of the layer.

If desired, in addition to, or in place of pigments or colorants, fanciful drawing patterns can be printed or otherwise imparted to the surface of any layer, but in particular to the top layer, to convey a desired visual aesthetic impression. This aesthetic impression is particularly achievable in the multi-layer nail enamel layer film embodiments of the present invention.

Each nail enamel layer of the nail film has one or more solvents residually from the manufacturing process, as previously mentioned. Thus, in the multi-layer nail enamel layer film embodiment, solvent is present in all nail enamel layers. The solvent prevents the layer, and, hence, the film, from drying out, thus ensuring its pliability and facilitating handling by the user.

Each nail enamel layer may have other optional ingredients. These ingredients include one or more thickeners or leveling agents, pearlescent agents, or glitters to give the desired effects.

The optional one or more thickeners or leveling agents include, but are not limited to, one or more clays including treated clays, treated or untreated silicas including fumed silicas, synthetic polymers, or a combination thereof. The one or more thickeners are present in an amount up to about 5 wt %, preferably up to about 1.5 wt %, based on the total weight of the nail enamel layer.

Preferably, the pearlescent agents and glitters, or any combinations thereof are present in an amount up to about 40 wt % based on the total weight of the nail enamel layer.

In the embodiments in which the nail film has two or more nail enamel layers, preferably three layers, the three layers are superimposed one on top of the other to impart a more fashionable nail polish, such as, for example, a French manicure.

In a preferred embodiment, the nail enamel film has an adhesive layer; a first or bottom or base coat layer in contact with the adhesive layer with the first nail enamel layer having one or more adjuvant film-forming polymers, pigments, fillers, and optionally one or more thickeners or leveling agents; a second or middle coat layer having one or more adjuvant film-forming polymers, and pigments; a top coat layer having the cross-linked polymer, and optionally glitters and/or pearlescent agents. As set forth above, each of these nail enamel layers has a residual amount of solvent. In this embodiment, the several nail enamel layers are preferred since the thickness of each layer can be decreased or minimized. Also, the thickener in the first nail enamel layer will even out any imperfectations, ridges or the like, in the nail. It is also preferred that a protective acetate resin layer overlies the top coat enamel layer.

In another embodiment, the nail film is the two nail enamel layer embodiment, noted above, and has an adhesive layer, a first coat layer and a top coat layer. The components of the first coat and top coat layers correspond to the description of the previous embodiment.

In yet another embodiment noted above, the nail film has an adhesive layer, and a single nail enamel layer.

In all embodiments, the nail enamel layer(s) are deposited on the substrate.

The nail film has a composite thickness preferably in the range from about 0.02 millimeter (mm) to about 1 mm, more preferably from about 0.02 mm to 0.5 mm, still more preferably from about 0.02 mm to about 0.1 mm, and most preferably from about 0.03 mm to about 0.1 mm. Preferably, each nail enamel layer has a thickness in the range from about 0.01 mm to about 0.50 mm. More preferably, each nail enamel layer has a thickness in the range from about 0.02 mm to about 0.35 mm, especially from about 0.02 to about 0.1 mm, and most preferably from about 0.02 mm to about 0.07 mm. Especially for multilayer nail enamel films, the nail enamel layer has a thickness in the range from about 0.03 mm to about 0.1 mm.

The set of fingernail/toenail coatings are provided for simple and inexpensive application to the nails and for an easier and quicker method to give the fashionable manicuring, including French manicure, without compromising quality.

The method of the present invention distinguishes over the disclosure of U.S. Pat. No. 4,903,840 to So (assignee) in part in that it employs the step of cross-linking the polymer. For example, the present method provides a substrate, and a nail enamel composition in liquid form capable of application to the substrate. The composition has a solvent as set forth above, a cross-linkable polymer, optionally a cross-linking agent, and optionally pigments, plasticizers, leveling agents, as described above with regard to the structure of the nail enamel strip. Also provided is a sprayable adhesive composition.

On the substrate, an adhesive material, followed by a nail enamel layer, are applied thereon. The nail enamel layer as applied from a die having one or more cross-linkable polymers, solvents and the other ingredients referred to above. A heating process is then applied to the nail enamel layer to substantially evaporate the solvent, although some residual solvent remains, as set forth above. Subsequently, the nail enamel layer incorporating the cross-linkable polymer to be cross-linked is exposed to UV light for cross-linking, which differs from the So patent above. As stated above, thermal energy may be used if a cross-linking agent is also used, although UV light is preferred.

This process is utilized iteratively for each of the nail enamel layers that are formed on the substrate. Generally, the last or topmost nail enamel layer is the layer that has the cross-linked polymer.

In all embodiments, the nail enamel strip is preferably sold in an enclosed, air-tight envelope or package. Preferably, the package is made of plastic. Also preferably, the package has therein an elongated master strip that has a number of preformed nail enamel films with perforations therebetween to provide for easy removal from the master strip. Each master strip is substantially flat. Each individual nail enamel film is in the shape of a fingernail, a toenail, or such other shapes as may be dictated by fashion or fad; as, for example, nail strips for a French manicure.

For application, the user removes a nail enamel strip from the master nail strip in the package, and removes the acetate protective barrier. The user then removes the nail enamel film from the substrate. The substrate is preferably furnished with a pull-off aid to facilitate its detaching. The end or edge of the nail enamel film is then trimmed to correspond precisely to the nail shape. Then, the nail enamel film is secured to the nail by pressing the nail enamel film firmly onto the nail.

It should be understood that the foregoing description is only illustrative of the present invention. Various alternatives and modifications can be devised by those skilled in the art without departing from the scope of the present invention. Accordingly, the present invention is intended to embrace all such alternatives, modifications and variances that fall within the scope of the appended claims.

What is claimed is:

1. A nail enamel strip comprising a substrate and a nail enamel film detachably adhered to said substrate, the film comprising: a transparent layer so that a base coat layer is visible with minimal loss in color when observed through the transparent layer, the transparent layer including a pre-cured cross-linked polymer comprising nitrocellulose, wherein said cross-linked polymer is UV cured; a film forming polyester polymer; an acrylates copolymer; a polyvinyl butyral film forming polymer; and a citrate ester plasticizer and/or a phthalate plasticizer.

2. A nail enamel strip comprising:

a substrate;

an adhesive layer; and a nail enamel film having one or more nail enamel layers, wherein one of said one or more nail enamel layers is a transparent layer so that a base coat layer is visible with minimal loss in color when observed through the transparent layer, the transparent layer having a pre-cured cross-linked polymer comprising a polymer selected from the group consisting of nitrocellulose, acrylic copolymer, polyamide and polyurethane, wherein said cross-linked polymer is UV cured, and wherein said nail enamel film is detachably adhered to said substrate;

wherein said nail enamel film is in the general shape of a human fingernail or toenail, and wherein said adhesive layer is disposed between said nail enamel film and said substrate so that upon detaching said substrate from said nail enamel film sufficient adhesive layer remains on said nail enamel film to adhere said nail enamel film to a human fingernail or toenail.

3. The nail enamel strip of claim 2, wherein said cross-linked polymer is nitrocellulose.

4. The nail enamel strip of claim 2, wherein said cross-linked polymer has film forming properties.

5. The nail enamel strip of claim 2, wherein said cross-linked polymer is present in an amount about 5 weight percent (wt %) to about 99 wt % based on the total weight of said nail enamel layer.

6. The nail enamel strip of claim 2, wherein said cross-linked polymer is present in an amount from about 20 wt % to about 99 wt % based on the total weight of said nail enamel layer.

7. The nail enamel strip of claim 2, wherein said cross-linked polymer is present in an amount from about 65 wt % to about 97 wt % based on the total weight of said nail enamel layer.

8. The nail enamel strip of claim 2, wherein the nail enamel strip has a thickness in a range from about 0.02 mm to about 1 mm.

9. The nail enamel strip of claim 2, wherein said one or more nail enamel layers has at least one nail enamel layer that has an adjuvant film-forming polymer.

10. The nail enamel strip of claim 9, wherein said adjuvant film-forming polymer is selected from the group consisting of nitrocellulose, polyacrylate homopolymer or copolymer, polyester, polyurethane, carbon-based resin, silicone resin, ethylcellulose, polyvinylbutyral, polyamide, polyester, and any combination thereof.

11. The nail enamel strip of claim 9, wherein said adjuvant film-forming polymer is present in an amount about 5 wt % to about 95 wt % based on the total weight of at least one nail enamel layer.

12. The nail enamel strip of claim 11, wherein said cross-linked polymer is present in the topmost layer in an amount of from about 65 wt % to about 97 wt % based on the total weight of the topmost layer.

13. The nail enamel strip of claim 2, wherein one of said one or more nail enamel layers has one or more pigments.

14. The nail enamel strip of claim 13, wherein said one or more pigments are selected from the group consisting of titanium dioxide, zirconium oxide and cerium oxide, zinc oxide, iron oxide, chromium oxide, ferric blue oxide, carbon black, barium lake, strontium lake, calcium lake or aluminum lake, mica, mica coated with pearlescent agent, mica coated with titanium oxide, mica coated with iron oxide, mica coated with natural pigment, mica coated with bismuth oxychloride, and any combinations thereof.

15. The nail enamel strip of claim 13, wherein said one or more pigments are present in the amount about 5 wt % to about 50 wt % based on the total weight of said pigment-containing layer.

16. The nail enamel strip of claim 2, further comprising an adhesive layer.

17. The nail enamel strip of claim 2, wherein said substrate has a pull-off aid.

18. The nail enamel strip of claim 2, wherein said one or more nail enamel layers is two nail enamel layers.

19. The nail enamel strip of claim 18, wherein each of said two nail enamel layers is present in an amount about 20 wt % to about 80 wt % of the total weight of said nail enamel film.

20. The nail enamel strip of claim 18, wherein said two nail enamel layers have one layer that is said topmost nail enamel layer with the cross-linked polymer therein.

21. The nail enamel strip of claim 20, wherein said two nail enamel layers have another layer that is a base coat layer with one or more pigments.

22. The nail enamel strip of claim 2, wherein said one or more nail enamel layers has at least one layer with one or more plasticizers therein.

23. The nail enamel strip of claim 22, wherein said one or more plasticizers are selected from the group consisting of citrate ester, phthalate, sulfonamide, and any combinations thereof.

24. The nail enamel strip of claim 2, wherein each of said one or more nail enamel layers has a residual solvent therein, and wherein said residual solvent is from about 1 wt. % to about 15 wt. % based on the total weight of said one or more nail enamel layers.

25. The nail enamel strip of claim 24, wherein said solvent is selected from the group consisting of methyl-, ethyl-, butyl-, amyl-, or 2-methoxyethyl acetate, methyl ethyl ketone, methyl isobutyl ketone, isopropyl acetate, toluene, xylene, p-xylene, hexane, heptane, aldehydes having 5 to 10 carbon atoms, ethers having 3 carbon atoms, lower alcohols, and any combination thereof.

26. The nail enamel strip of claim 2, wherein said one or more nail enamel layers has at least one nail enamel layer that has one or more optional ingredients selected from the group consisting of a thickener, pearlescent agents, glitters, and any combination thereof.

27. The nail enamel strip of claim 2, wherein the nail strip is packaged in an airtight envelope.

28. A method for making nail enamel strips comprising the steps of:

providing a substrate;

depositing sequentially an adhesive layer, and then a nail enamel layer composition having one or more nail enamel layers, such that said adhesive layer is disposed between said substrate and said nail enamel layer composition, wherein said nail enamel layer composition has a transparent layer so that a base coat layer is visible with minimal loss in color when observed through the transparent layer, the trans parent layer including a cross-linkable polymer comprising a polymer selected from the group consisting of nitrocellulose, acrylic copolymer, polyamide and polyurethane, and a solvent;

heating said nail enamel layer composition; and

UV curing the cross-linkable polymer to form a cross-linked polymer; wherein said nail enamel layer composition is in the general shape of a human fingernail or toenail.

29. The method of claim 28, wherein said nail enamel layer composition has a pigment.

30. A method of applying a nail enamel film that has a transparent layer so that a base coat layer is visible with minimal loss in color when observed through the transparent layer, the transparent layer including a cross-linked polymer comprising a polymer selected from the group consisting of nitrocellulose, acrylic copolymer, polyamide and polyurethane, on nails comprising the steps of:

detaching the nail enamel film from a substrate that supports said nail enamel film, wherein an adhesive layer is disposed between said nail enamel film and said substrate, and wherein the pre-cured cross-linked polymer is UV cured, and wherein said nail enamel film is in the general shape of a human fingernail or toenail;

applying said nail enamel film on a surface of a human nail wherein said adhesive layer secures said nail film to said surface of a human nail;

cutting said nail enamel film to more closely conform to the shape of the human nail, and allowing the nail enamel film to dry completely, wherein said nail enamel film requires no UV curing after application.

* * * * *